(12) United States Patent
Nevo

(10) Patent No.: US 10,702,251 B2
(45) Date of Patent: Jul. 7, 2020

(54) CRYOGENIC BIOPSY SYSTEM AND METHOD

(71) Applicant: ROBIN MEDICAL INC, Baltimore, MD (US)

(72) Inventor: Erez Nevo, Baltimore, MD (US)

(73) Assignee: ROBIN MEDICAL INC., Baltimore, MD (US)

( * ) Notice: Subject to any disclaimer, the term of this patent is extended or adjusted under 35 U.S.C. 154(b) by 1120 days.

(21) Appl. No.: 14/745,511

(22) Filed: Jun. 22, 2015

(65) Prior Publication Data

US 2015/0305722 A1  Oct. 29, 2015

Related U.S. Application Data

(63) Continuation-in-part of application No. 13/581,311, filed as application No. PCT/IB2011/050805 on Feb. 25, 2011, now Pat. No. 9,566,047.

(60) Provisional application No. 62/014,712, filed on Jun. 20, 2014, provisional application No. 61/307,884, filed on Feb. 25, 2010.

(51) Int. Cl.
| | |
|---|---|
| *A61B 10/00* | (2006.01) |
| *A61B 10/02* | (2006.01) |
| *A61B 18/02* | (2006.01) |
| *A61B 10/04* | (2006.01) |
| *A61B 18/00* | (2006.01) |

(52) U.S. Cl.
CPC ...... *A61B 10/0275* (2013.01); *A61B 10/0096* (2013.01); *A61B 10/04* (2013.01); *A61B 18/02* (2013.01); *A61B 2010/045* (2013.01); *A61B 2018/00642* (2013.01); *A61B 2018/00714* (2013.01); *A61B 2018/00791* (2013.01); *A61B 2018/0293* (2013.01)

(58) Field of Classification Search
CPC . A61B 10/0275; A61B 18/02; A61B 10/0096; A61B 10/04; A61B 2018/0293; A61B 2018/00791; A61B 18/0218
See application file for complete search history.

(56) References Cited

U.S. PATENT DOCUMENTS

| | | | |
|---|---|---|---|
| 4,888,956 A * | 12/1989 | le Roux Murray | F25C 1/00 62/51.1 |
| 6,551,255 B2 | 4/2003 | Van Bladel et al. | |
| 2002/0087152 A1* | 7/2002 | Mikus | A61B 17/3421 606/21 |
| 2003/0069571 A1* | 4/2003 | Treat | A61B 18/085 606/29 |
| 2005/0113854 A1 | 5/2005 | Uckele | |
| 2007/0055173 A1 | 3/2007 | DeLonzor et al. | |
| 2007/0191732 A1 | 8/2007 | Voegele | |

(Continued)

*Primary Examiner* — Sean P Dougherty
*Assistant Examiner* — David Joseph Fernandez-Fidalgo
(74) *Attorney, Agent, or Firm* — Daniel J. Swirsky; Ricki L. Simon; AlphaPatent Associates Ltd.

(57) ABSTRACT

A cryogenic biopsy device is configured to provide tissue samples that are partially frozen and partially non-frozen. This enables histopathology analysis of the intact non-frozen part of the tissue sample and assessment of the in-vivo biomolecular state of the tissue that is stabilized and maintained in the frozen part of the sample. The device of the present invention may be used in rigid instruments and in flexible devices, such as endoscopes, for example, and may be suitable for single use or multiple use.

10 Claims, 17 Drawing Sheets

(56) References Cited

U.S. PATENT DOCUMENTS

2008/0026420 A1 1/2008 Rimm et al.
2011/0224576 A1 9/2011 Jackson et al.

* cited by examiner

CRYOGENIC BIOPSY SYSTEM AND METHOD

CROSS-REFERENCE TO RELATED APPLICATIONS

The present application claims the benefit of U.S. Provisional Patent Application No. 62/014,712, filed Jun. 20, 2014, and is also a continuation-in-part of U.S. patent application Ser. No. 13/581,311, filed on Aug. 26, 2012, which is a U.S. National Phase Application under 35 U.S.C. 371 of PCT International Application No. PCT/IB2011/050805, which has an international filing date of Feb. 25, 2011, and which claims priority from U.S. Provisional Patent Application No. 61/307,884, filed Feb. 25, 2010, the contents of all of which applications are incorporated herein by reference in their entireties.

FIELD OF THE INVENTION

The present invention relates to a cryogenic biopsy system and method, and more particularly to a system and method for preserving the viability and integrity of a biopsy tissue sample.

BACKGROUND OF THE INVENTION

Molecular medicine holds much promise for advancing cancer diagnosis and treatment if biomarkers, molecular targets and drug effects on these targets can be accurately assessed in tumors. The amount and function of molecular drug targets within signal transduction pathways are often regulated by rapid enzymatic reactions in response to physiological stimuli. Biopsies play a central role in assessing biomarkers and molecular targets in solid tumors, but the traumatic process of cutting tissue samples by current biopsy devices perturb the tumor environment and thereby induce extraneous and confounding molecular responses to tissue trauma, bleeding and ischemia. Expeditious processing of the biopsy specimen using snap freezing or rapid fixation following tissue harvesting may be ineffective for preventing many rapid enzymatic modifications, because time frames of biopsy procedures and tissue handling before they are processed in the lab are longer than that of the enzymatic reactions. Commonly used chemical stabilization of the tissue, for example by formalin, kills the cells and degrades many of the cellular ingredients such as proteins, DNA, RNA, peptides and other molecules.

A method for tumor biopsy that preserves the molecular profile may facilitate pharmacodynamic assessment of targeted therapeutics and may also enable individualized molecular therapy of solid tumors based on accurate information about signal transduction pathways, molecular drug targets and biomarkers. This can maximize the efficacy of new directed chemotherapy agents by choosing the most appropriate patients for each type of therapy. As most of these therapies are associated with severe adverse effects and are highly expensive, individually directed therapy may eliminate suffering in patients that will not benefit from these therapies and can substantially reduce healthcare costs.

Many cancer patients do not benefit from the systemic treatments they receive. For example, an adjuvant chemotherapy regimen that is considered highly effective may often improve the disease-free or overall survival rate by only a few percent. Also, chemotherapy for metastatic disease often provides sustained benefit for a small portion of the patients treated. Therefore, the medical therapies currently available to clinical practice expose far more patients than will benefit to the cost and toxicity of these agents. Although this over treatment is understandable in dealing with life-threatening diseases, the ability to better personalize treatment decisions could have important benefits for patients as well as reduce medical costs.

Biomarkers can be classified into two classes based on their mode of analysis: 1. Histology-based biomarkers adhere to specific structures in the tissue (e.g. cell membranes, chromosomes) and thus require intact tissue (e.g. immunohistochemical (IHC) and fluorescent in-situ hybridization (FISH)). In these tests tissue fixation can be done by chemicals (e.g. formalin-fixed paraffin-embedded, FFPE) or by freezing (e.g. frozen sections). However, freezing adversely affects the ultrastructure of the tissue and cells due to formation of ice crystals, and as such, optical microscopy should be done on fresh or on FFPE tissue samples. These techniques can identify single or groups of cancerous cells in otherwise healthy tissue and may enable early detection of cancer. 2. Content-based biomarkers are determined as the tissue concentration of specific molecules (e.g. proteins, peptides, RNA and DNA, metabolites) that either have altered structure (e.g. DNA alterations) or abnormal levels in tumor cells. These biomarkers do not require the use of intact tissue, and typically involve tissue homogenate that is achieved by sample pulverization in the lab. It would be advantageous to have a biopsy system which enables preservation of biomarkers as well as preservation of the tissue and cellular ultrastructure that provide the basis for histopathology analysis of stained tissue by high magnification microscopy.

A cryogenic biopsy device is disclosed in U.S. Pat. No. 6,551,255. The device is configured for securing and coring of tumors within the body. An adhesion probe provides a coolant for adhering to the tumor and easing attachment of the tumor to the probe. However, the device disclosed therein does not disclose a system and method for providing samples of tissue which may be analyzed histologically as well as via biomarker analysis while maintaining the molecular profile of the sample.

Furthermore, while pathologists use frozen tissue for rapid intraoperative diagnosis, there are limitations to what can be seen in frozen tissue during detailed histologic evaluation. For example, retraction artifacts in tissue that has been frozen might cause problems in the assessment of invasion and in the differential diagnosis of lymphovascular invasion. Also, nuclear details that are needed for tumor grading are lost by ice crystal formation in frozen tissue. These problems may exist in any tissue that has ever been frozen even if it has been immediately fixed in formalin. While freezing the tissue in-situ, before it is cut by the biopsy device, maintains the in-vivo biomarker profile of the tissue and enables histology-based biomarker tests like IHC and FISH, it is not acceptable for detailed histopathology diagnosis. Thus there is a need for a system and method for harvesting and preservation of tissue samples that maintains the fine structural details of the tissue and intracellular components on one hand and the in-vivo biomolecular profile on the other hand.

SUMMARY OF THE INVENTION

There is provided, in accordance with embodiments of the present invention, a cryogenic biopsy device that enables differential cooling of the tissue to achieve a frozen part and a non-frozen part in the same biopsy sample. The device includes a cryogenic needle having a needle tip configured to penetrate a tissue to be sampled and configured to freeze the tissue, a cutting cannula coaxial to the cryogenic needle, configured to cut a sample of the tissue via a rotation or translation motion, and a collection compartment for collecting the sample tissue and preserving the sample with a temperature gradient so one part of the sample is frozen and another part is non-frozen.

In accordance with further features in embodiments of the present invention, the cryogenic needle may have a diameter of 1.5 mm or less, or of any other suitable diameter. The cryogenic needle further includes a hollow portion for introduction of a freezing gas therein. According to further features, the device may further include a sensor or multiple sensors at the needle tip. The sensor or multiple sensors in some embodiments may be a temperature sensor or other sensors—biochemical, optical—that monitor the tissue properties.

In accordance with further features in embodiments of the present invention, the actuation mechanism may be a gear mechanism with a pinion and wheel configuration. The gear mechanism may also include a threaded bar attached to the wheel, and positioned through a nut on the device body. The threaded bar may rotatably pass through the nut upon activation of the gear mechanism. The gear mechanism is configured to provide rotational and translational movement of the cutting cannula simultaneously. Another actuation mechanism can be based on a loaded spring mechanism that rapidly advances the cutting cannula in a translation motion when released.

In accordance with further features in embodiments of the present invention, the collection compartment may be formed by the cryogenic needle and the cutting cannula. The tissue sample in such a compartment will have a thick walled cylindrical shape. In accordance with other embodiments, the collection compartment may be a notch in an outer compartment surrounding the cryogenic needle. In some embodiments, the cutting cannula is a thin-walled, sharpened cylinder that enables tissue cutting through a translation motion. Alternatively, cutting may be achieved by a rotating cannula with saw-like edge. The body of the device as well as the cryogenic needle may be flexible for use in an endoscope, for example.

There is provided, in accordance with another embodiment of the present invention, a biopsy system. The system includes a processor having a freezing unit and a temperature gradient generator, a cryogenic needle in fluid or gas communication with the freezing unit, a cutting apparatus positioned coaxial to the cryogenic needle for cutting frozen or partial frozen samples of tissue, and a collection compartment for collecting the sample of tissue, wherein the collection compartment is configured to maintain all the sample or part of the sample in a frozen state.

In accordance with further features in embodiments of the present invention, the freezing unit may include a freezing substance compartment and a processor. In some embodiments, the system further includes a sensor positioned on the cryogenic needle, wherein the sensor is in electronic communication with the processor and is configured to provide feedback to the processor. The processor may be configured to regulate the tissue temperature based on the feedback from the sensor.

In accordance with further features in embodiments of the present invention, the tissue sample is maintained with a temperature gradient in the sample, so part of it is frozen and part of it is maintained at low temperature above the freezing temperature of the tissue. The desired temperature gradient can be achieved by proper positioning of the collection compartment in reference to the cooling focus of the cryogenic needle—tissue near the cooling focus will be frozen, while tissue away from the focus will have a temperature above the freezing temperature of the tissue. Alternatively, a temperature gradient may be maintained in the tissue by keeping the cryogenic needle at a low temperature below the tissue's freezing point (e.g. −10 degrees Celsius) and keeping the cutting cannula at a high temperature above the tissue's freezing point (e.g. +10 degrees Celsius). This will generate a temperature gradient in a radial direction, with the portion of the tissue sample adjacent to the cryogenic needle in a frozen state while the portion of the tissue sample adjacent to the cutting cannula is in a non-frozen state. In some embodiments, a heating element is included within or on the device to help maintain the temperature gradient.

In some embodiments, the frozen part is maintained at a temperature of −10 degrees Celsius or less.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The above and further advantages of the present invention may be better understood by referring to the following description in conjunction with the accompanying drawings in which.

Figure 1A:
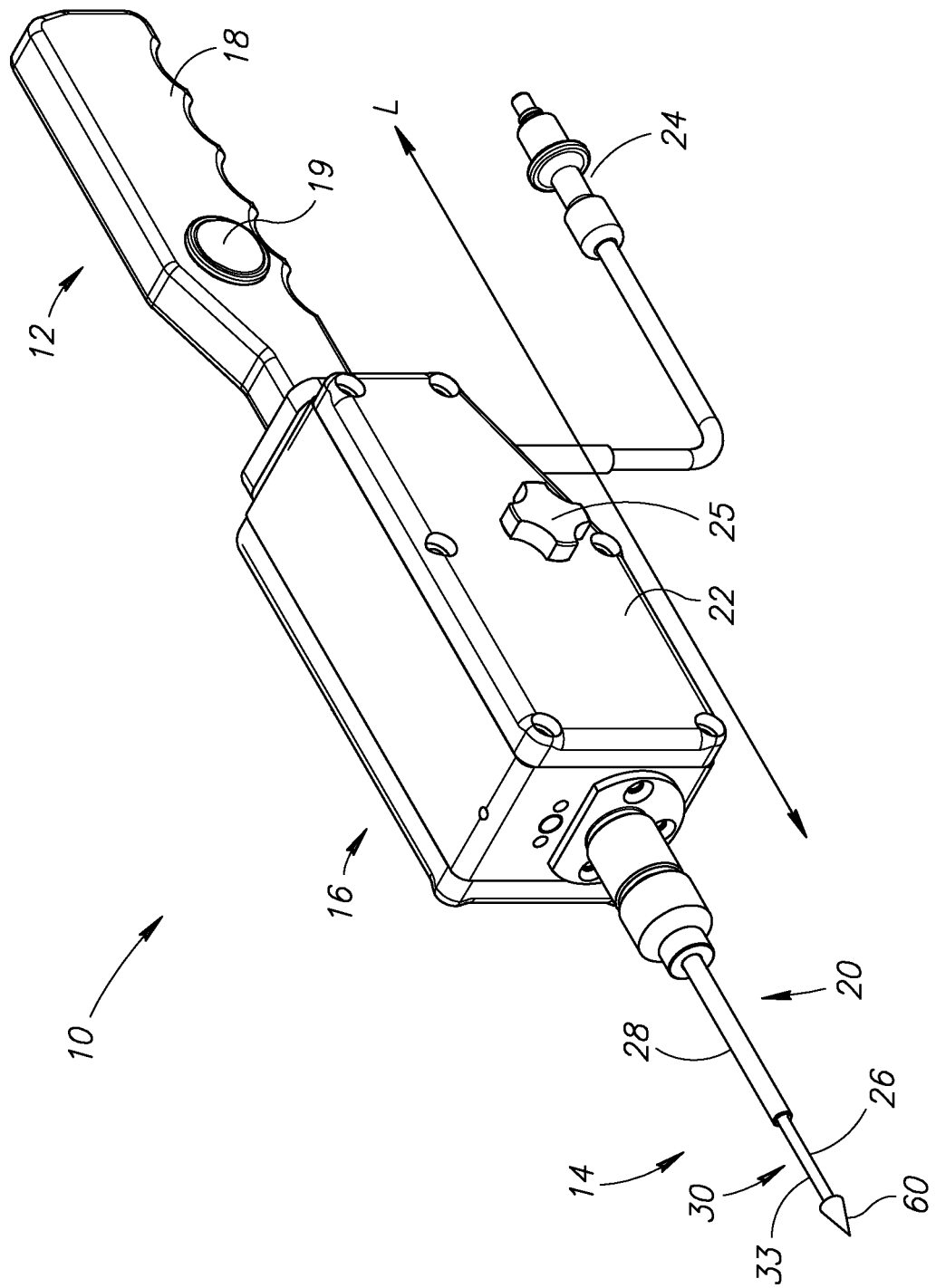
FIGS. 1A-1C are schematic illustrations of a biopsy device in accordance with embodiments of the present invention.

It will be appreciated that for simplicity and clarity of illustration, elements shown in the drawings have not necessarily been drawn accurately or to scale. For example, the dimensions of some of the elements may be exaggerated relative to other elements for clarity or several physical components may be included in one functional block or element. Further, where considered appropriate, reference numerals may be repeated among the drawings to indicate corresponding or analogous elements. Moreover, some of the blocks depicted in the drawings may be combined into a single function.

DETAILED DESCRIPTION OF THE INVENTION

In the following detailed description, numerous specific details are set forth in order to provide a thorough understanding of the present invention. It will be understood by those of ordinary skill in the art that the present invention may be practiced without these specific details. In other instances, well-known methods, procedures, components and structures may not have been described in detail so as not to obscure the present invention.

Embodiments of the present invention are directed to systems and methods for biopsy and preservation of a tissue sample, and more particularly to a cryogenic biopsy device. The device and method of the present invention are designed to provide samples which can be used for both microscopic histopathology analysis and biomarker analysis. The principles and operation of systems and methods according to the present invention may be better understood with reference to the drawings and accompanying descriptions.

Before explaining at least one embodiment of the present invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein are for the purpose of description and should not be regarded as limiting.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

A device in accordance with embodiments of the present invention is a cryogenic biopsy device that can snap-freeze the tissue and maintain the whole sample or part of the sample in a deep-frozen state until it reaches the pathology lab for further processing. The device of the present invention may be used in rigid instruments and in flexible devices, such as endoscopes, for example, and may be suitable for single use or multiple use.

The present invention aims to stabilize tissue biomarkers based on rapid, deep freezing of the tissue. To eliminate any change due to the traumatic cutting action itself, the deep-freeze of the tissue is done in-situ, before tissue harvesting, by using a cryogenic device. Tissue freezing within a few seconds stabilizes all cellular biochemical processes and ensures stabilization of protein-, RNA- and DNA-based biomarkers.

The use of a cryogenic biopsy device, such as the one described herein, provides better results than conventional biopsy procedures for assessing highly dynamic molecular profiles that are associated with a high degree of instability due to tissue injury. It also preserves cellular viability and keeps its ingredients intact, as opposed to commonly used chemical tissue stabilization, for example by formalin, which kills the cells, degrades the tissue and modifies proteins, peptides, DNA and RNA strands, and many other ingredients.

Moreover, the cryogenic biopsy device of the present invention can be used to provide a sample which is frozen in one portion of the tissue and non-frozen in another portion of the tissue so as to enable preservation of biomarkers as well as preservation of the tissue and cellular ultrastructure.

Figure 1B:
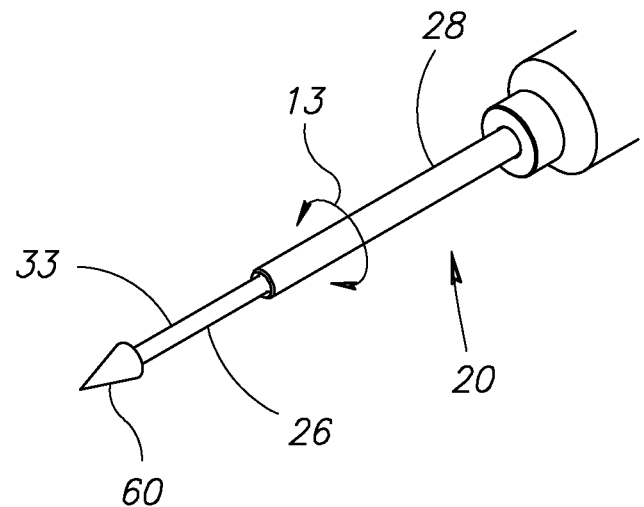
Figure 1C:
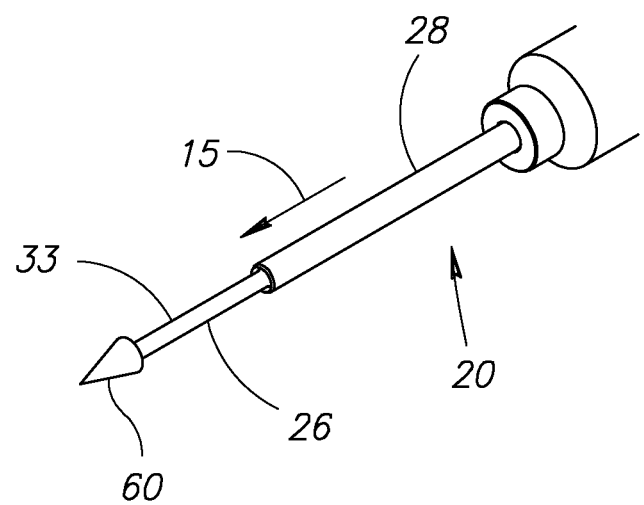

Reference is now made to FIG. 1A, which is a schematic illustration of a biopsy device 10 in accordance with embodiments of the present invention. Device 10 has a proximal end 12, a distal end 14, and a middle portion 16 connecting proximal end 12 to distal end 14. Distal end 14 is defined as the portion of device 10 which enters the body and contacts the tissue to be biopsied. Proximal end 12 is defined as the portion of device 10 which is outside of the body and closest to the user. Proximal end 12 includes a handle 18 for holding of device 10 and may further include an activation switch 19. Distal end 14 includes a cutting portion 20, which will be described in greater detail hereinbelow. In some embodiments, middle portion 16 has a housing 22 which houses a mechanism for operation of cutting portion 20. A port 24 is positioned proximal to middle portion 16, and is used to connect a cryogenic needle 26 to a freezing unit, as will be described in greater detail with reference to FIG. 5. Cryogenic needle 26 includes a body portion 33 and a tip portion 60 at a distal end thereof. Cutting portion 20 includes a cutting cannula 28 coaxially positioned and movable with respect to cryogenic needle 26, and is designed to cut the tissue sample. Cutting portion 20 further includes a collection compartment 30 for holding a tissue sample therein during the procedure and as device 10 is removed from the body. Cutting portion 20 may include a rotatable cutting mechanism, as shown in FIG. 1B and as indicated by arrow 13, or a translational cutting mechanism, as shown in FIG. 1C and as indicated by arrow 15, or cutting portion 20 may be a combination of a rotatable and a translational cutting mechanism. Alternatively, cutting portion 20 may be any suitable mechanism for cutting tissue.

Figure 2:
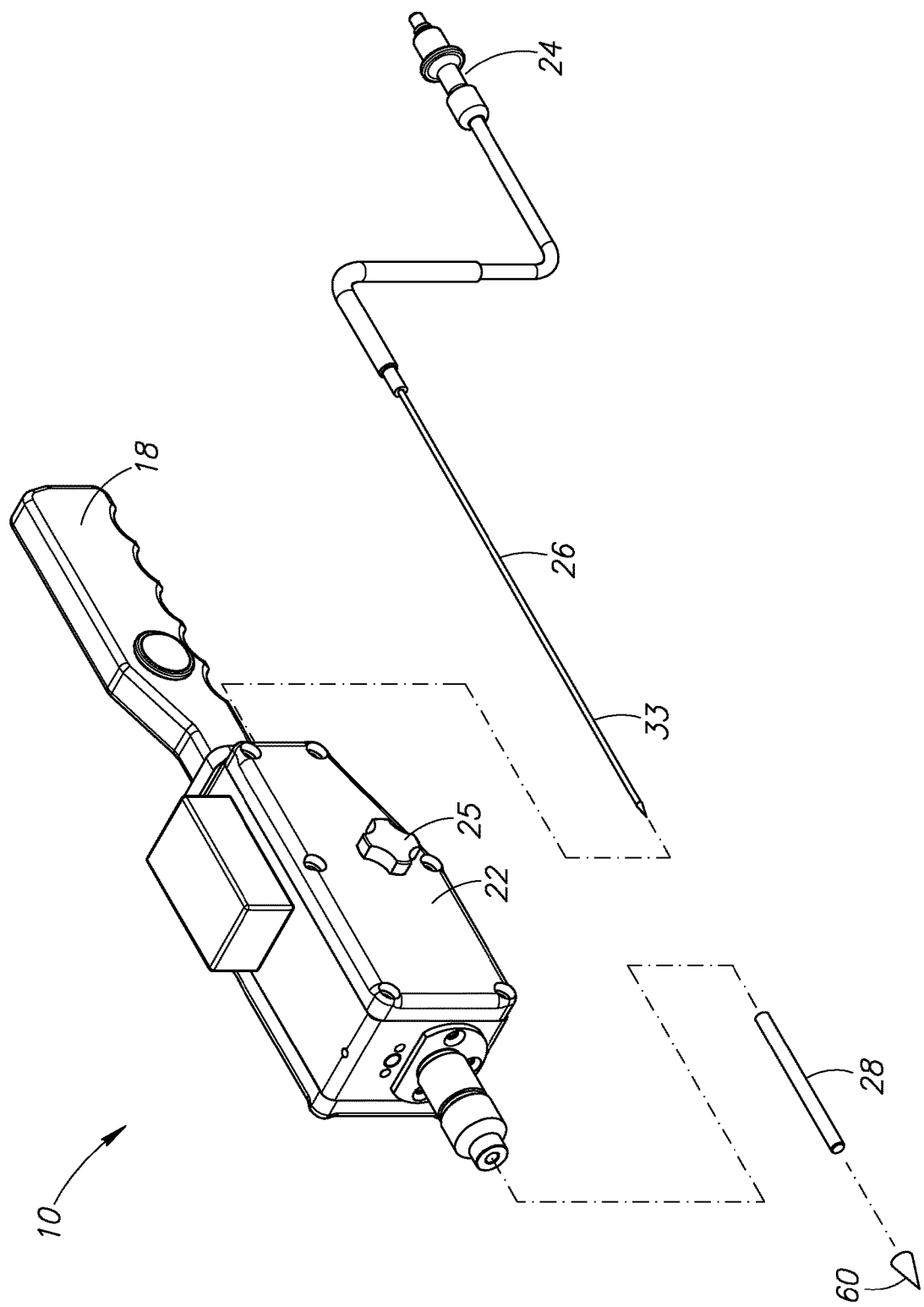
FIG. 2 is a schematic illustration of the device of FIG. 1A, shown with portions removed to further illustrate these portions of the device.

Reference is now made to FIG. 2, which is a schematic illustration of the device of FIG. 1A, shown with port 24, cryogenic needle 26, needle tip portion 60, and cutting cannula 28 removed, to further illustrate these portions of device 10. Port 24 allows for introduction of a freezing substance to cryogenic needle 26. Cryogenic needle 26 may be, for example, a clinical grade 17-gauge cryotherapy needle (Galil Medical, Inc., Arden Hills, Minn.), having a diameter of approximately 1.5 mm. In some embodiments, cryogenic needle 26 is another commercially available needle or may be constructed specifically for the present invention. In some embodiments, a smaller diameter cryogenic needle may be used. For example, a cryogenic needle having a diameter of 0.3-0.4 mm would allow the overall size of device 10 to be in a range of 17-18 Gauge. In other embodiments, a larger diameter cryogenic needle 26 may be used. Cryogenic needle 26 may be any size needle suitable for a cryogenic biopsy procedure. Needle tip portion 60 of cryogenic needle 26 is configured to penetrate the tissue to be sampled.

Cryogenic needle 26 may be secured in position by a fastener 25. Fastener 25 may be, for example, a knob or a snap ring. In the embodiments shown herein, fastener 25 is positioned on housing 22. However, it should be readily apparent that fastener 25 may be positioned in any suitable location on device 10. Fastener 25 may be used to secure cryogenic needle 26 during the procedure and may be released thereafter when the harvested tissue is removed from device 10.

Figure 3A:
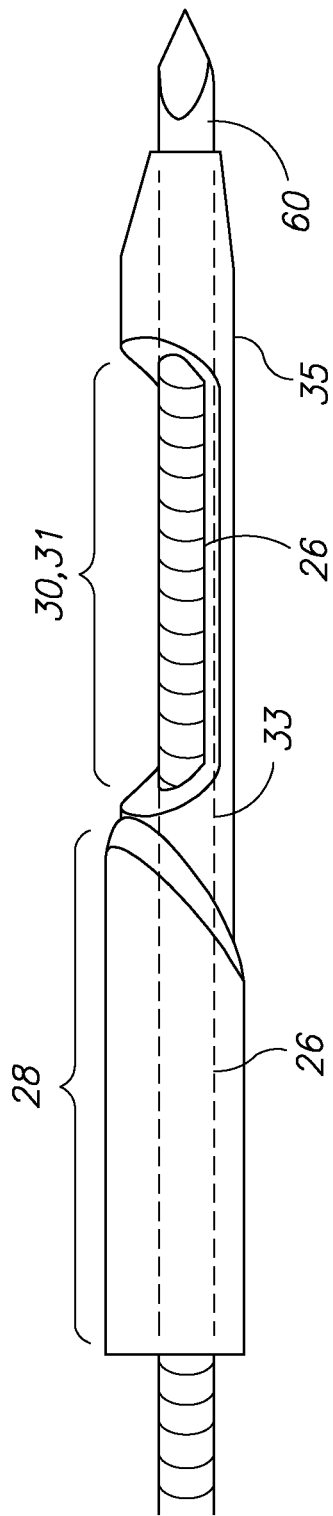
FIGS. 3A-3B are schematic illustrations of a collection compartment of the device of FIGS. 1A-1C, in accordance with embodiments of the present invention.
Figure 3B:
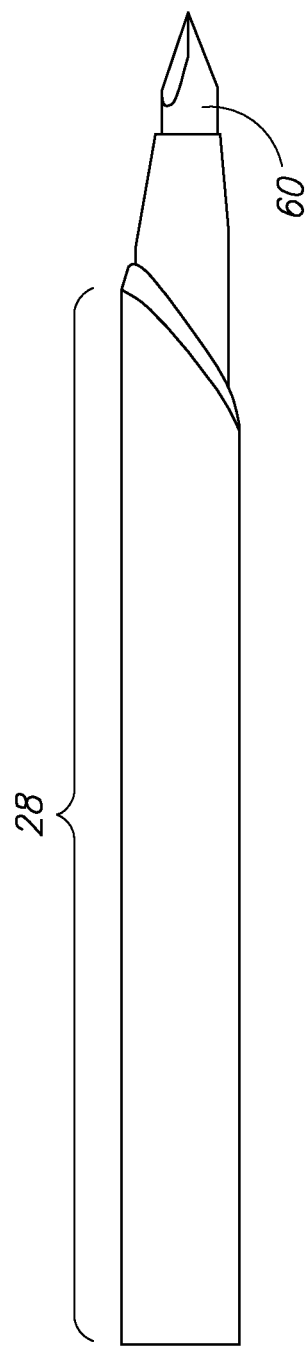

Reference is now made to FIGS. 3A-3B, which are illustrations of a portion of device 10 depicting collection compartment 30, in accordance with embodiments of the present invention. As shown in FIG. 3A, an outer compartment 35 is positioned around body portion 33 of cryogenic needle 26. Collection compartment 30 is formed via a notch 31 within outer compartment 35. In some embodiments, outer compartment 35 is comprised of a plastic sleeve which is configured to surround cryogenic needle 26 and provide heat insulation around collection compartment 30. Collection compartment 30 is enveloped by cutting cannula 28 as cutting cannula 28 moves forward and/or rotates to cut the frozen tissue, until it stops at the needle tip portion 60. Thus, as shown in FIG. 3A, notch 31 in outer compartment 35 is proximal to needle tip portion 60. Cutting cannula 28 is shown in a proximal position in FIG. 3A, and in a distal position in FIG. 3B, wherein in FIG. 3B, cutting cannula 28 is positioned over collection compartment 30. In the embodiment depicted in FIGS. 3A-3B, forward motion of cutting cannula 28 results in slicing of the tissue sample that is within collection compartment 30. The forward motion can be achieved, for example, by a gear mechanism that moves cutting cannula 28 either in a translational movement alone, or with a combined rotational and translational movement as explained below with reference to FIGS. 4A and 4B, or by a loaded spring mechanism as described with reference to FIG. 4C, or by any other suitable mechanism.

Figure 4A:
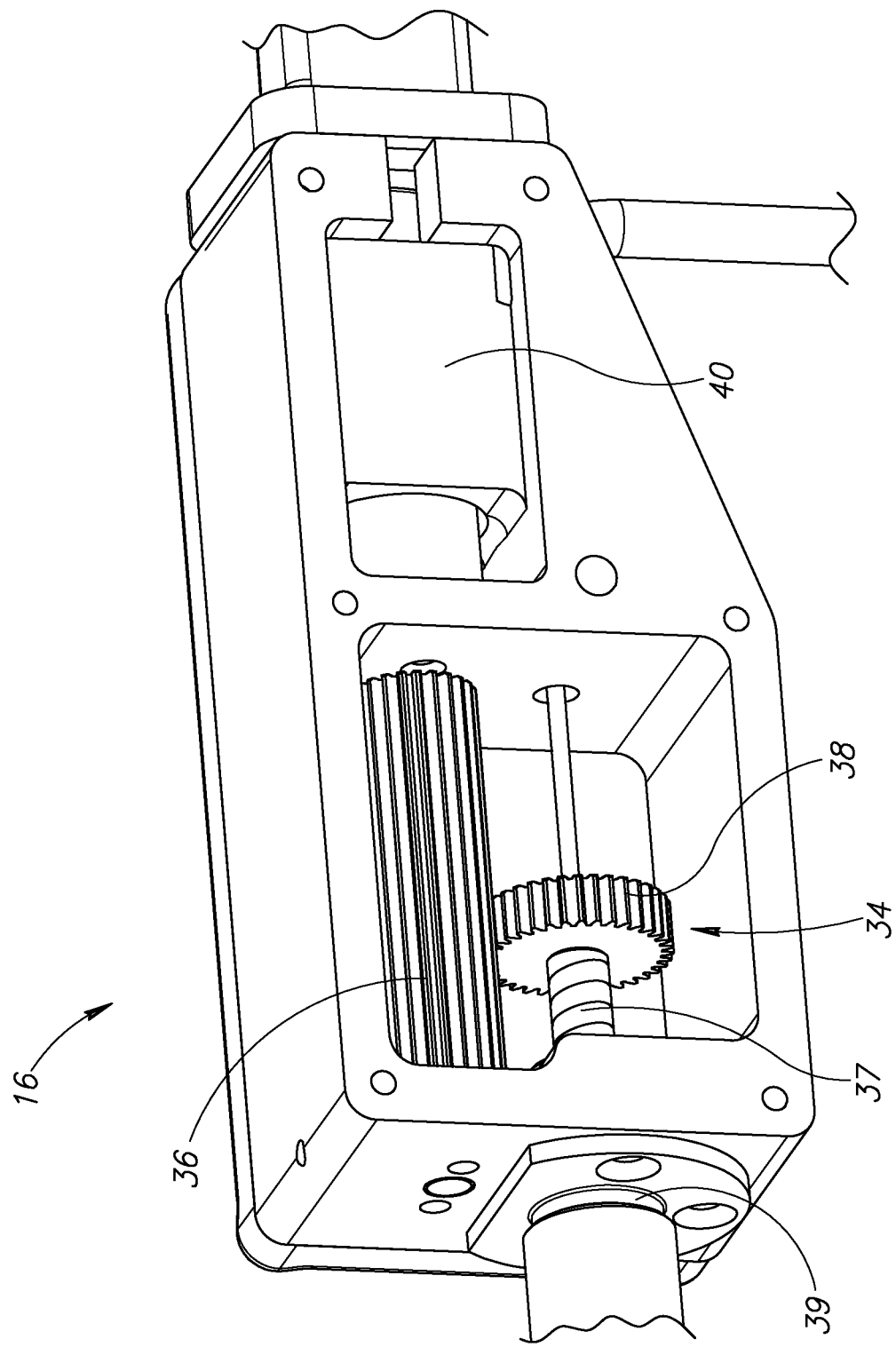
FIGS. 4A and 4B are perspective views of a middle portion of the device of FIG. 1, in accordance with embodiments of the present invention.
Figure 4B:
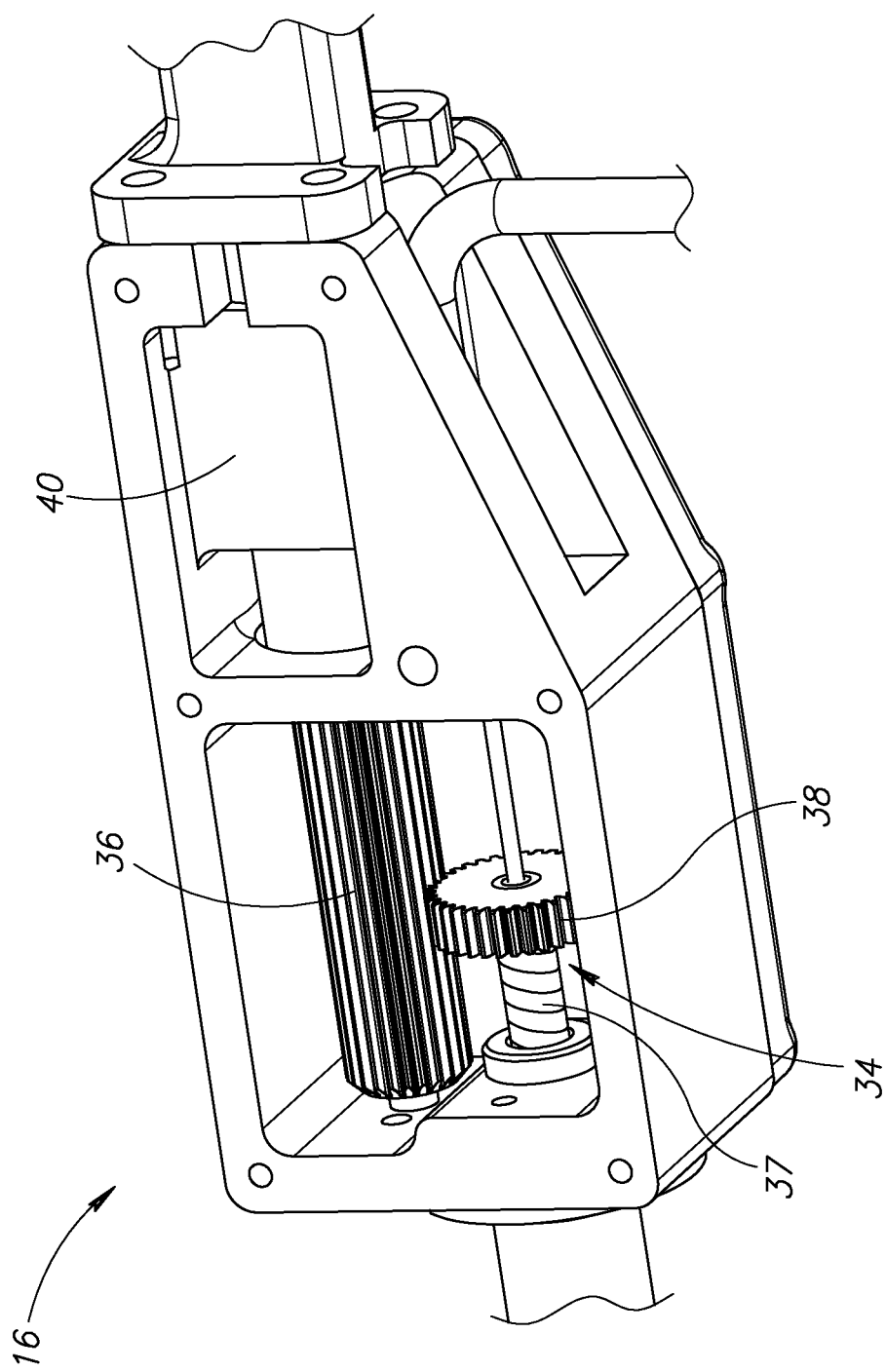

Reference is now made to FIGS. 4A and 4B, which are perspective views of middle portion 16 of device 10, in accordance with one embodiment of the present invention. Side portions of housing 22 have been removed to reveal an inner mechanism of middle portion 16. Middle portion 16 includes an actuation mechanism, which in the present embodiment is a gear mechanism 34 having a pinion 36 and wheel 38 configuration. Further, wheel 38 is attached to a threaded bar 37. Threaded bar 37 is distal to wheel 38, and is positioned through a nut 39 which is attached to a distal portion of housing 22. Threaded bar 37 is at a proximal end of cutting cannula 28. In one embodiment, threaded bar 37 is attached to a proximal end of cutting cannula 28. In another embodiment, threaded bar 37 and cutting cannula 28 comprise a unit, wherein threaded bar 37 comprises a proximal end of cutting cannula 28. The disclosed configuration provides for translational motion at the same time and with the same mechanism as rotational motion. The speed of rotation and sizes of grooves on pinion 36 and wheel 38 determine a fixed relationship between the translational motion and rotational motion. In an alternative embodiment, a separate translational mechanism may be used, and translational and rotational movement may be separately controlled. It should be readily apparent that any other suitable gear mechanism may be used. In the embodiment shown herein, the gear mechanism is a combination rotational/translational mechanism, such that activation of gear mechanism 34 causes rotation and forward motion of cutting cannula 28. Cryogenic needle 26 remains static while cutting cannula 28 rotates and advances. A driving module 40 is housed in middle portion 16 and drives the pinion to generate the rotation and advancement of the slicer. Driving module 40 may be, for example, an electrical motor.

Figure 4C:
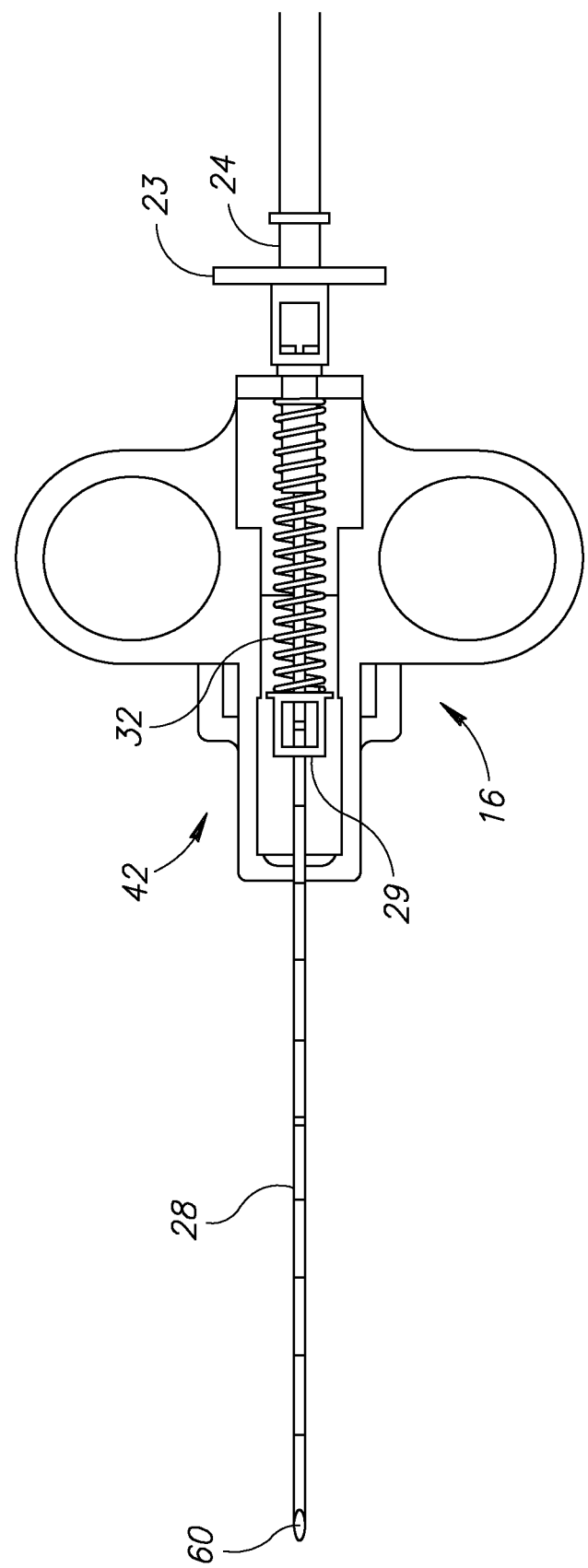
FIG. 4C is a schematic illustration of a cryogenic biopsy device in accordance with additional embodiments of the present invention, including a spring-loaded cutting cannula for cutting of a sample therein.

Reference is now made to FIG. 4C, which is a schematic illustration of middle portion 16 of device 10, in accordance with additional embodiments of the present invention. In the embodiment shown in FIG. 4C, the actuation mechanism is a spring mechanism 42 including a loaded spring 32, which pushes cutting cannula 28 forward when released. Prior to inserting cryogenic needle 26 into the body, spring mechanism 42 is cocked by pulling knob 23 in a proximal direction in order to load spring 32 until a plastic latch (not shown), for example, is engaged to hold spring 32 in a loaded state. Spring 32 is attached to cutting cannula 28, for example by an adapter 29, so that when spring 32 is pulled back proximally during the cocking step, collection compartment 30 is exposed. In order to activate the cutting mechanism, the latch is released by a trigger mechanism (not shown), spring 32 returns to the unloaded state and pushes cutting cannula 28 forward to cut the biopsy sample and cover collection compartment 30.

In some embodiments, device 10 may be comprised of a flexible material, thereby providing a flexible cryogenic biopsy device for use through an endoscope, for example. Cryogenic needle 26 may be flexible as well.

Figure 5:
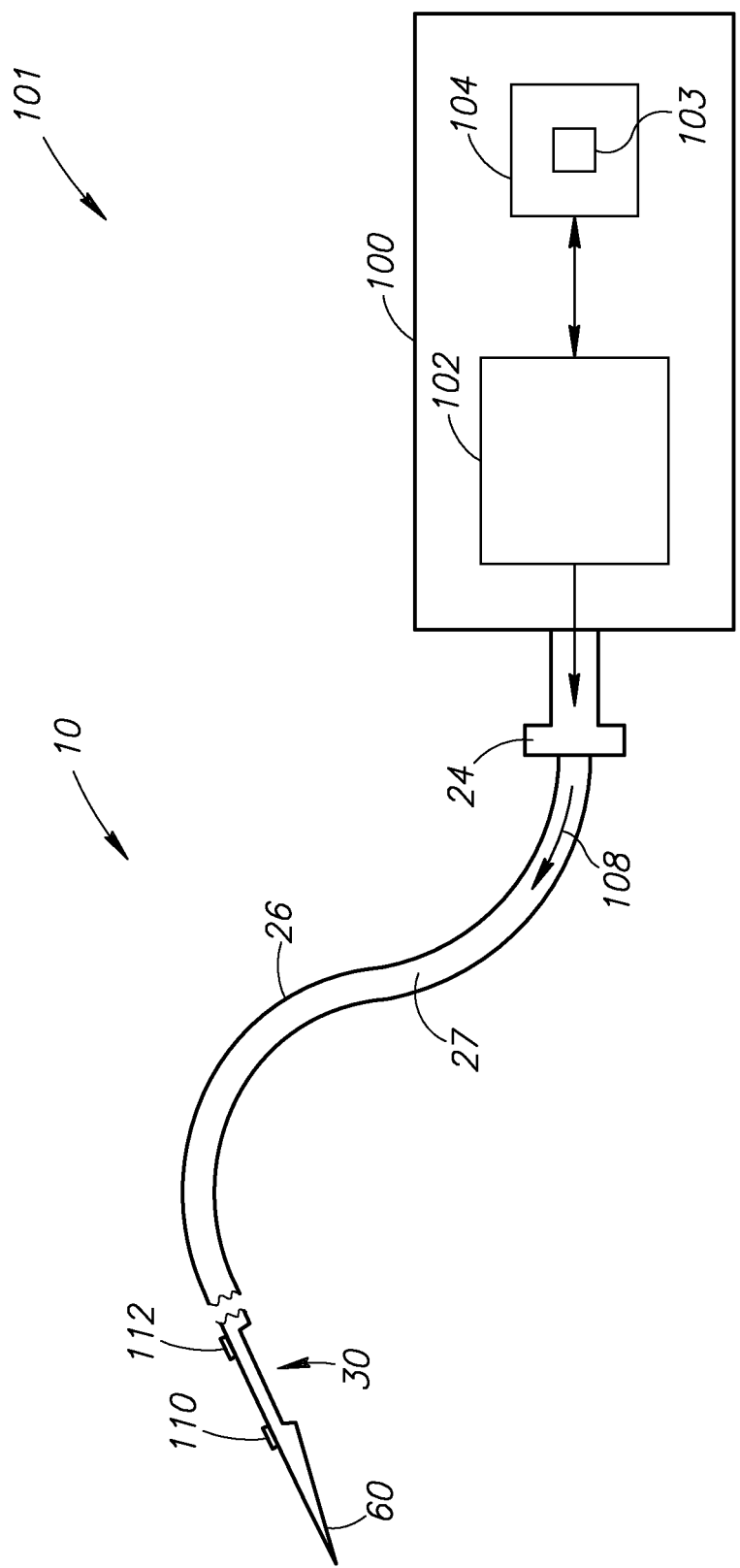
FIG. 5 is a partially block-diagram and partially schematic illustration of a system including the device of FIG. 1A and a freezing unit, in accordance with embodiments of the present invention.

Reference is now made to FIG. 5, which is a partially block-diagram and partially schematic illustration of a cryogenic biopsy system 101 in accordance with embodiments of the present invention. System 101 includes cryogenic biopsy device 10 and a temperature control unit 100. In the embodiment shown herein, temperature control unit 100 is an external unit which is connected to cryogenic needle 26 via port 24. In other embodiments, temperature control unit 100 may be incorporated within cryogenic biopsy device 10. In the embodiment shown in FIG. 5, cryogenic needle 26 has a hollow portion 27 therethrough, through which a freezing substance may be inserted, as indicated by arrow 108. Temperature control unit 100 may include a freezing substance compartment 102 and a processor 104. In some embodiments, processor 104 further includes a temperature gradient generator 103, as will be described in further detail hereinbelow with reference to FIGS. 11 and 12. Freezing substance compartment 102 is configured to hold a freezing substance, such as Argon gas, for example. The freezing substance is introduced through port 24 into cryogenic needle 26. Optionally, processor 104 may regulate an amount and flow rate of freezing substance to enable control of the tissue freezing process (e.g. rate and magnitude of temperature drop). In some embodiments, a first sensor 110 may be positioned at needle tip portion 60 near or within collection compartment 30. First sensor 110 may be in electronic communication with processor 104, and may be used to provide feedback regarding temperature of the tissue in collection compartment 30. In additional embodiments, first sensor 110 may be any other type of sensor, including biochemical, optical, etc. Based on feedback from sensor 110, processor 104 can make adjustments regarding the amount of freezing substance to release or the rate of release or other parameters. Thus, processor 104 may ensure that only part of the tissue sample is maintained in a frozen state while another part of the tissue is maintained in a non-frozen state. Alternatively, processor 104 may maintain the entire tissue sample in a frozen state, or may be configured to change the temperature dynamically at different points in the process. In some embodiments, a second sensor 112 may be positioned at another location in reference to collection compartment 30. For example, first sensor 110 may be positioned distal to collection compartment 30 and second sensor 112 may be positioned just above collection compartment 30. Alternatively, second sensor 112 may be positioned proximal to collection compartment 20. It should be readily apparent that any suitable configuration for first and second sensor 110 and 112 are included within the scope of the invention. Second sensor 112 may also be in electronic communication with processor 104, and may be used to provide additional feedback regarding temperature or other measurable parameters of the tissue sample in collection compartment 30 to enable better control of the temperature or a temperature gradient in collection compartment 30. In some embodiments, more than two sensors may be used. In some embodiments, a heating element may also be included on device 10 and may be in electrical communication with processor 104 in order to provide a temperature gradient in a sample within collection compartment 30, as will be described in greater detail hereinbelow.

Figure 6A:
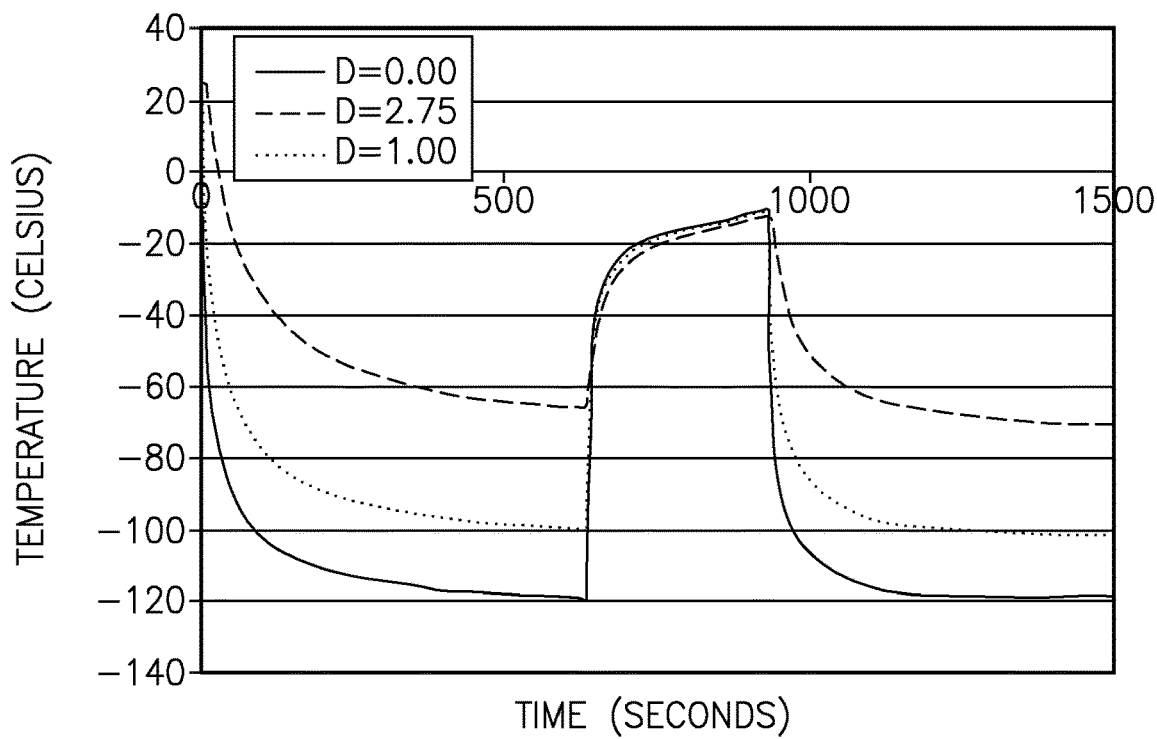
FIGS. 6A and 6B are graphical illustrations of temperature curves at distances from a needle surface.
Figure 6B:
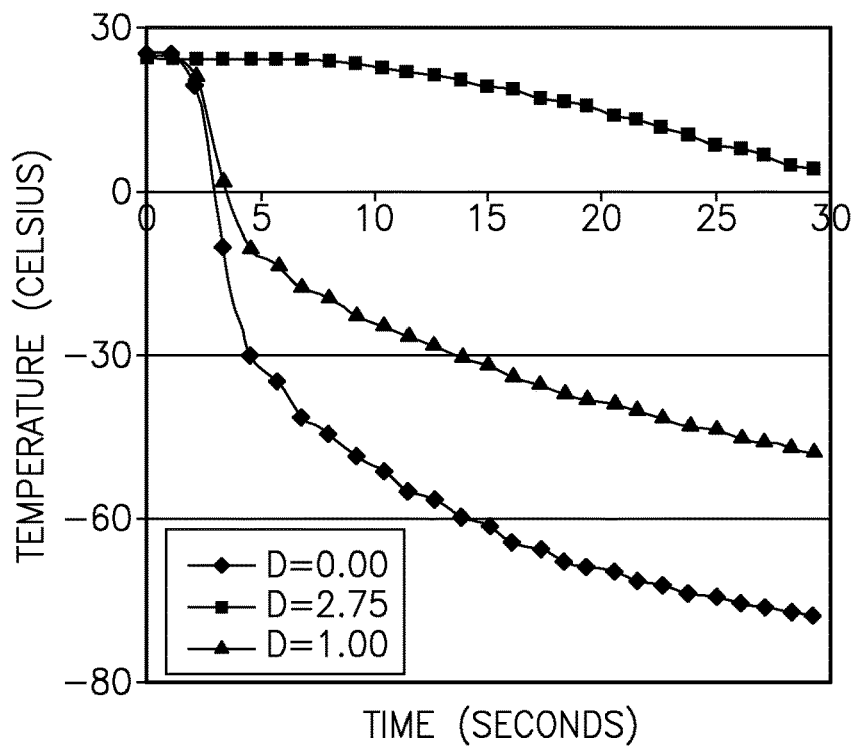

Tissue should be frozen to a temperature of −10 to −50 degrees Celsius in order to sufficiently preserve the biomolecular processes of the tissue. Tissue freezing to a temperature of −30° C. can be achieved at a distance of 1 mm from the surface of cryogenic needle 26 within approximately 15 seconds by commercially available cryo-ablation apparatus (e.g. SeedNet system, Galil Medical, Inc., Arden Hills, Minn.). Reference is now made to FIGS. 6A and 6B, which are graphical illustrations of temperature curves at distances from a needle surface. These measurements were made by Galil Medical using a cryo-ablation needle such as the one disclosed for use in the cryogenic biopsy device of the present invention. As shown in FIG. 6A, temperature curves at the needle surface and at a distance of 2.75 mm from the surface were measured. As shown in FIG. 6B, a temperature curve at a distance of 1 mm from the surface was interpolated from the two measured curves. At a temperature of −30° C., which is around the eutectic point of the intracellular and extracellular fluids, all intracellular biochemical processes cease and biomarker levels stabilize.

Freezing may be done by using compressed Argon gas through the Joule-Thomson effect to produce extremely low temperatures (−130° Celsius at the surface of cryogenic needle 26), or by other gases (e.g. Nitrogen, CO2, NO, air). As the gas passes through cryogenic needle 26, an iceball is formed around at least a portion of cryogenic needle 26, which stabilizes the intra-cellular biomolecular processes of the tissue. The portion of cryogenic needle at which an iceball is formed is defined as an area of cryogenic focus. The area of cryogenic focus may be, for example, at or near needle tip portion 60. In other embodiments, the area of cryogenic focus may be at other portions of cryogenic needle 60, or may be evenly distributed along a length of cryogenic needle. It should be readily apparent that any type of cryogenic method is included within the scope of the invention, including introduction of gases such as Nitrogen, Argon, CO2, electric cooling (e.g. Peltier cooler), hydraulic cooling with low temperature fluid or any other suitable method. The relative position of the area of cryogenic focus in the cryogenic needle and the tissue sample compartment 30 enables the generation of a temperature gradient along the tissue sample in order to maintain part of it frozen (close to the area of cryogenic focus) and part of it non-frozen (away from the area of cryogenic focus).

Figure 7A:
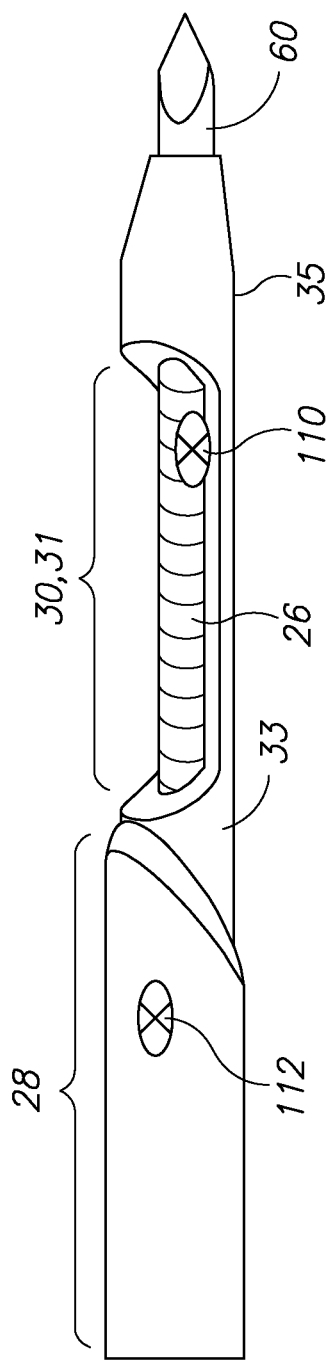
FIGS. 7A-7E are schematic illustrations of the collection compartment of FIGS. 3A-3B, configured for providing a temperature gradient, in accordance with embodiments of the present invention.

In embodiments of the present invention, cryobiopsy device 10 is configured to provide a temperature gradient in the tissue sample, so that one part of the tissue sample is frozen while another part of it is non-frozen. Reference is now made to FIGS. 7A-7E, which are illustrations of collection compartment 30 configured to produce a temperature gradient, in accordance with embodiments of the present invention. As shown in FIG. 7A, collection compartment 30 is formed by notch 31 in outer compartment 35, proximal to needle tip portion 60. Cutting cannula 28 is shown in a proximal position in FIG. 7A, and in a distal position in FIG. 7B, wherein in FIG. 7B, cutting cannula 28 is positioned over collection compartment 30. In the embodiment shown in FIG. 7C, the area of cryogenic focus is at a distal end 64 of collection compartment 30, close to needle tip portion 60. As such, temperature T increases along the length of collection compartment 30, from the lowest point (e.g. −10 degrees Celsius) at distal end 64 to the highest point (e.g. +10 degrees Celsius) at a proximal end of collection compartment 30. If properly controlled, cryogenic biopsy device 10 can be operated so the tissue at distal end 64 of collection compartment 30 is frozen, while the tissue at the proximal end of collection compartment 30 is non-frozen. The tissue at the center area of the compartment 30 may have an intermediate temperature and can be either frozen or non-frozen, depending on the temperature settings.

Figure 7B:
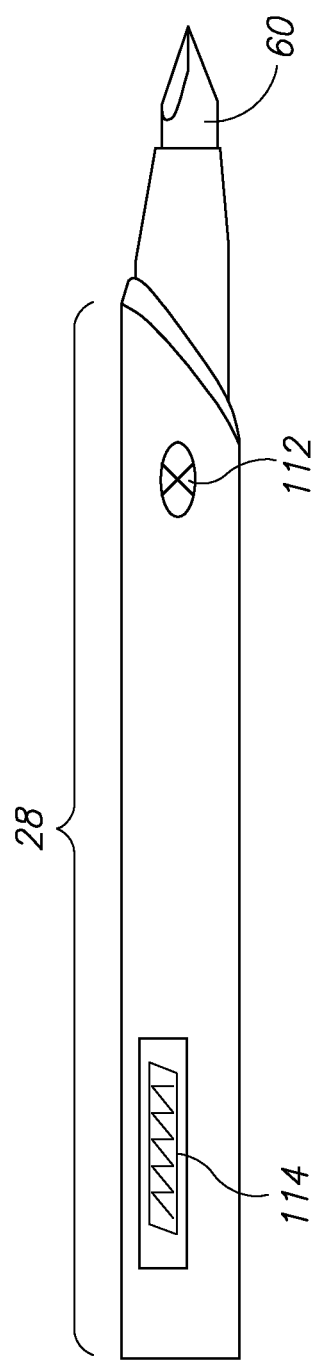
Figure 7C:
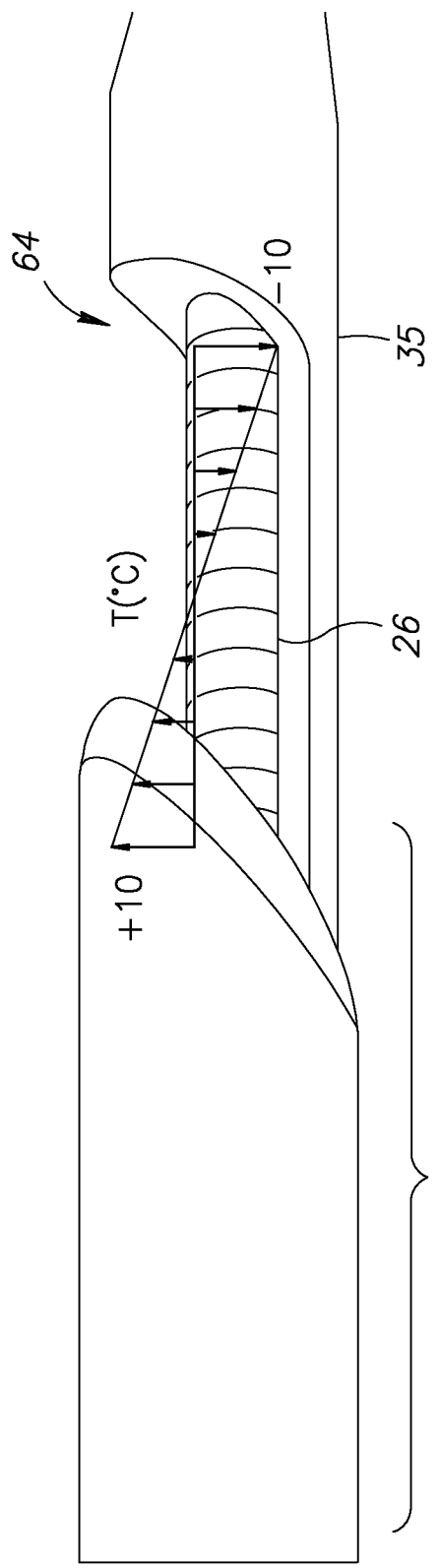

In the embodiments shown in FIGS. 7A-7E, in order to control the temperature gradient, also known as differential cooling, of the tissue sample, first sensor 110 is positioned within collection compartment 30. In the embodiment shown herein, first sensor 110 is positioned on cryogenic needle 26 within notch 31 at a distal end of notch 31. In some embodiments, a second temperature sensor 112 is positioned on cutting cannula 28 at a distal end thereof, and proximal to first temperature sensor 110. As shown in FIG. 7B, in some embodiments, a heating element 114 is positioned on cutting cannula 28, proximal to second sensor 112. Heating element 114 may be formed, for example, from an electrical resistive wire such as manufactured by Alloy Wire International Ltd., UK. It should be readily apparent that all or some of first sensor 110, second sensor 112, and heating element 114 may be attached to or embedded within the body of device 10, and the locations of these elements may be varied as well. Processor 104 of system 101 receives feedback from first sensor 110, which is configured to measure a parameter, such as temperature for example, of the frozen part of a sample positioned within collection compartment 30, and from second sensor 112, which is configured to measure a parameter (such as temperature) of the non-frozen part of the sample. Processor 104 controls the operation of either or both of freezing substance compartment 102 and heating element 114 based on feedback from first and second sensors 110 and 112 to maintain the frozen part of the sample in a frozen state and to maintain the non-frozen part of the sample in a non-frozen state. Heating element 114 may be positioned in close proximity to the collection compartment 30 to enable independent control of the temperature of the non-frozen part of the tissue sample.

Figure 7D:
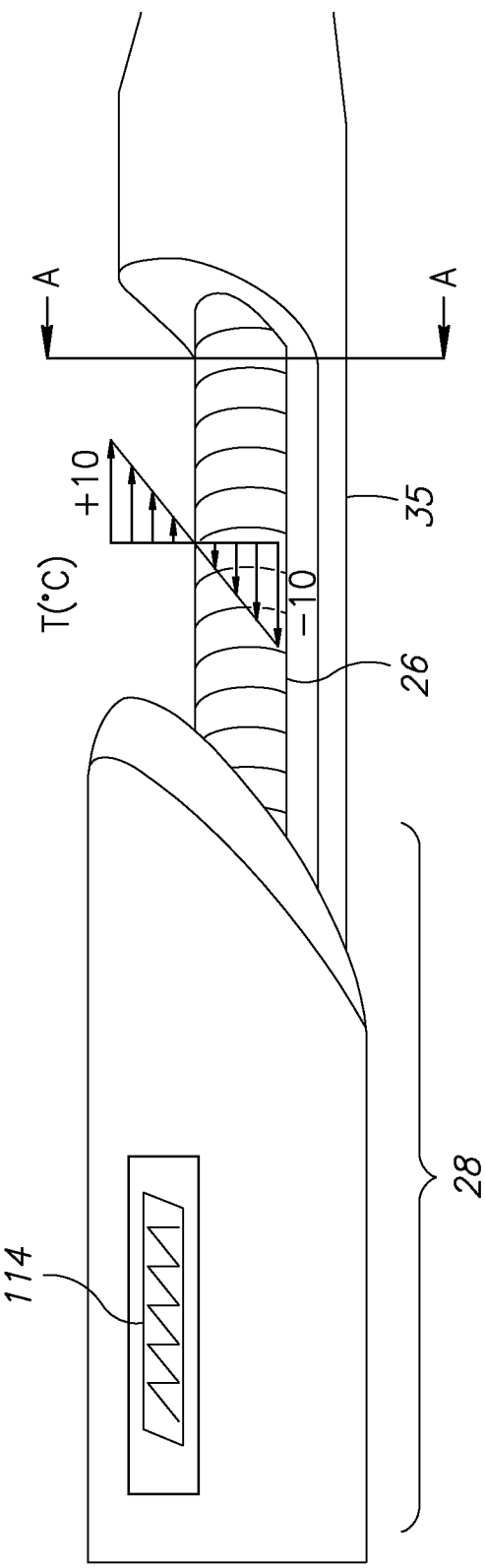
Figure 7E:
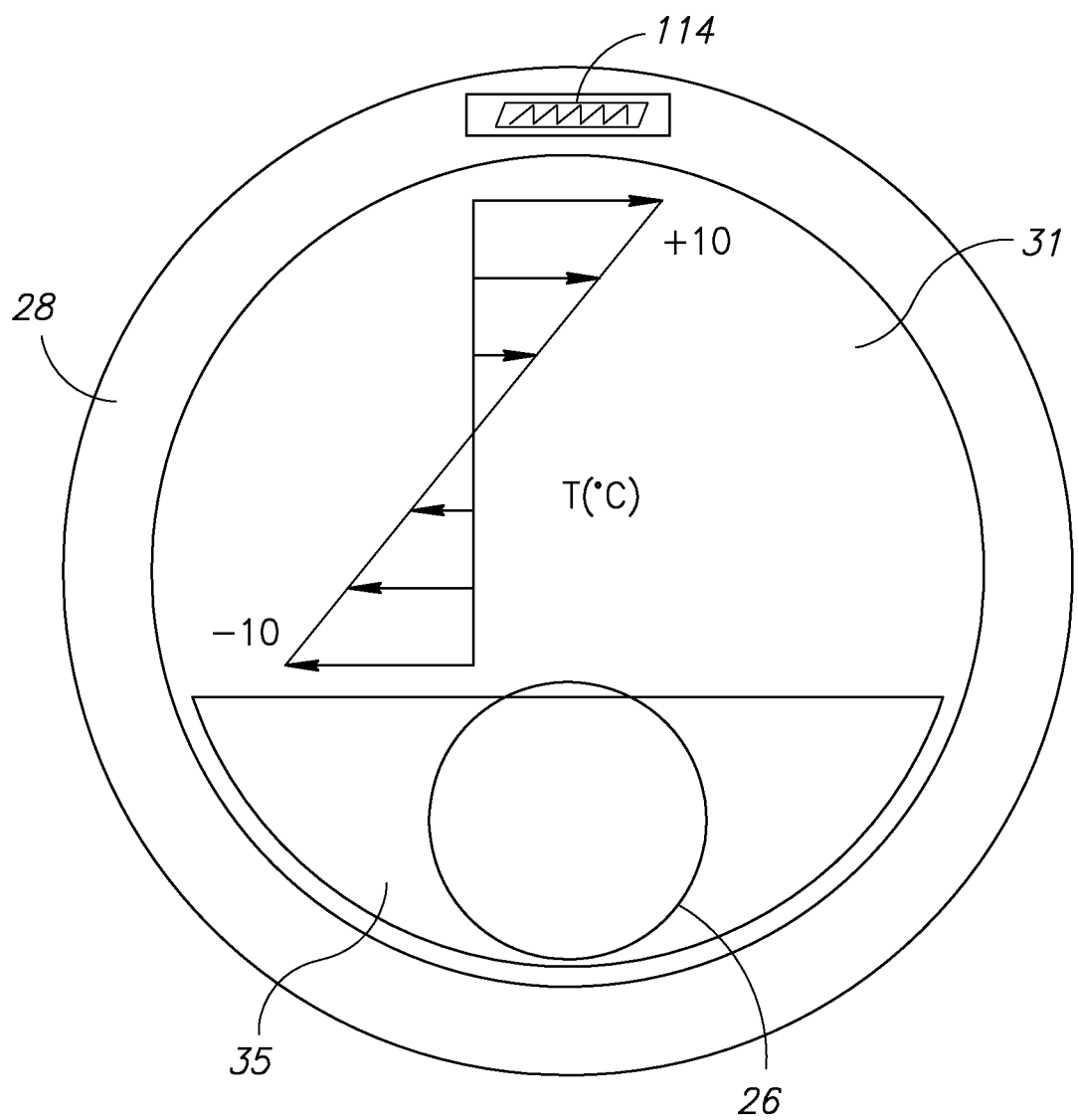

In the embodiment shown in FIGS. 7D and 7E, which are longitudinal and cross-sectional (section A-A as indicated in FIG. 7D) illustrations, respectively, the temperature T is configured to increase across the height of collection compartment 30, wherein tissue close to a bottom portion of notch 31 is frozen by the cryogenic needle while tissue close to cannula 28, at a top portion of notch 31, is maintained at a higher, non-frozen temperature due to cannula 28 being heated by heating element 114.

Figure 8A:
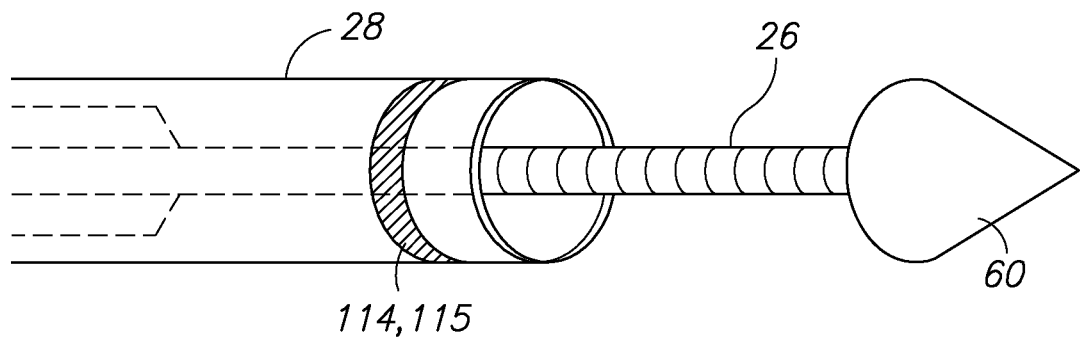
FIGS. 8A and 8B are schematic illustrations of a collection compartment of the device of FIGS. 1A-1C, configured for providing a radial temperature gradient in a tissue sample, in accordance with additional embodiments of the present invention.
Figure 8B:
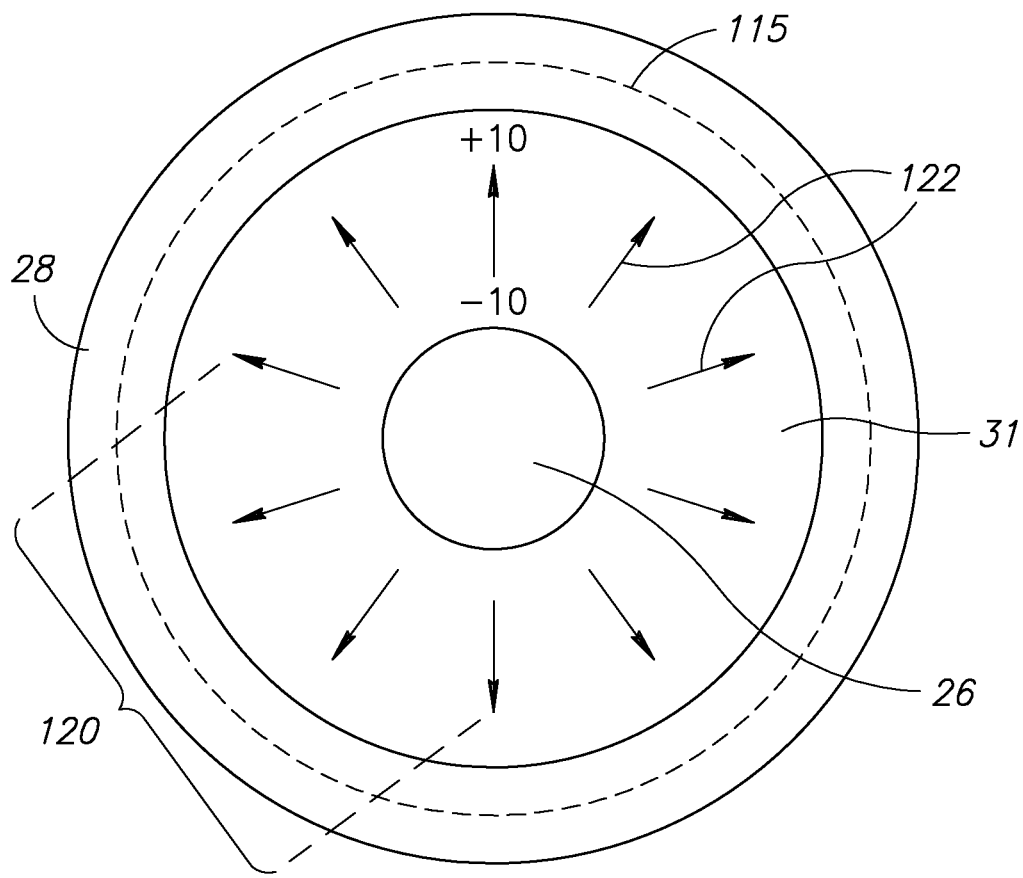

In some embodiments, a radially oriented gradient may be formed. Reference is now made to FIG. 8A, which is an illustration of device 10 in accordance with embodiments of the present invention, wherein heating element 114 is a circumferential heating element 115 which is configured to produce a radially oriented gradient. In this embodiment, heating element 114 may be, for example, a heating wire, such as manufactured by Alloy Wire International Ltd., UK. The heating wire may be embedded into cutting cannula 28 circumferentially to form circumferential heating element 115, and is configured to maintain the outer part of a tissue sample 120 at a temperature above the freezing point (e.g. +10 degrees Celsius). As shown in FIG. 8B, since the inner part of the tissue sample is maintained in a frozen state due to cooling by cryogenic needle 26, a temperature gradient is generated in tissue sample 120 in a radial direction, as depicted schematically by arrows 122.

Figure 9A:
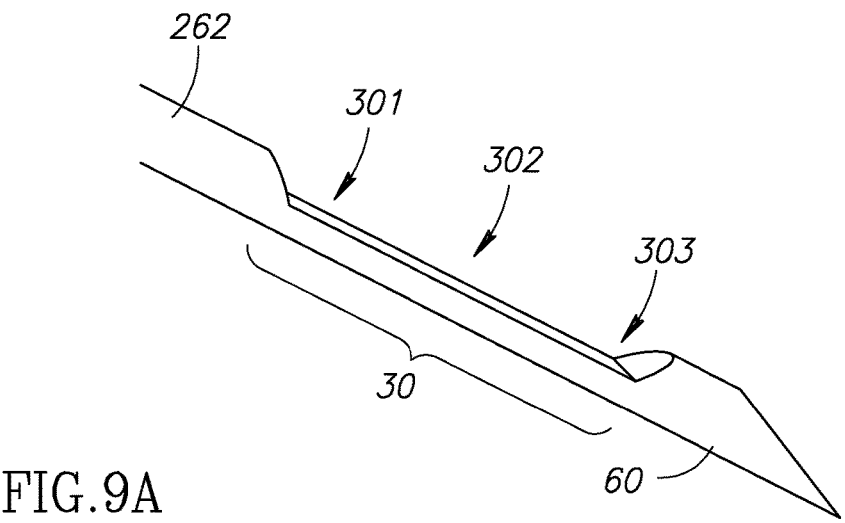
FIGS. 9A and 9B are schematic and graphical illustrations, respectively, of measured changes in temperature in a tissue sample as a function of distance from an area of cryogenic focus along a length of the collection compartment of FIGS. 3A-3B, over time.
Figure 9B:
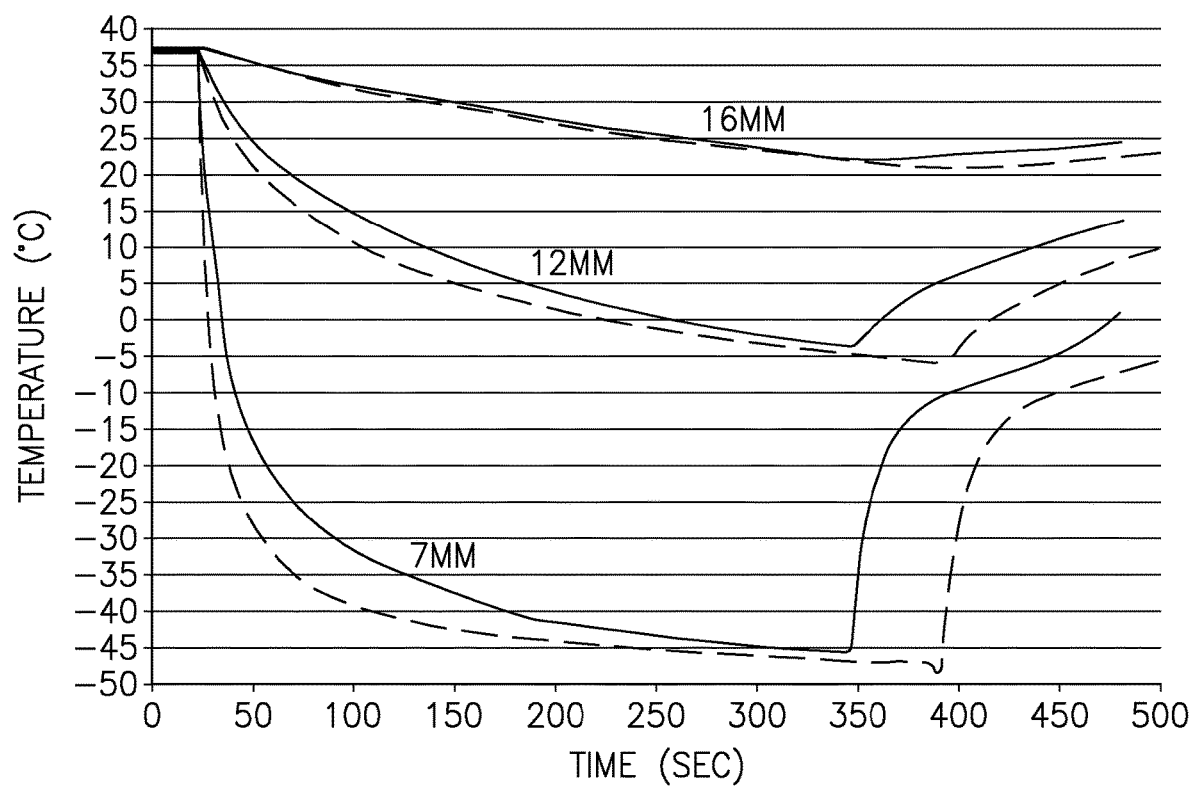

Reference is now made to FIGS. 9A and 9B, which are schematic and graphical illustrations showing another distribution of the temperature in a tissue sample as a function of distance from an area of cryogenic focus at a proximal end 262 of collection compartment 30 over time. As shown in FIG. 9A, measurements were taken at distances of 7 mm (as shown in reference number 301), at 12 mm (reference number 302) and at 16 mm (as shown in reference number 303) from the area of cryogenic focus at the proximal end 262 of collection compartment 30. As shown in FIG. 9B, the temperature in the tissue sample within collection compartment 30 increases as a function of the distance from the proximal end 262, with temperature below the tissue freezing point in the compartment end 301 that is 7 mm away and with higher temperatures above the freezing point in positions 302 (12 mm away from the cryogenic apparatus) and 303 (16 mm away) along collection compartment 30.

Figure 10:
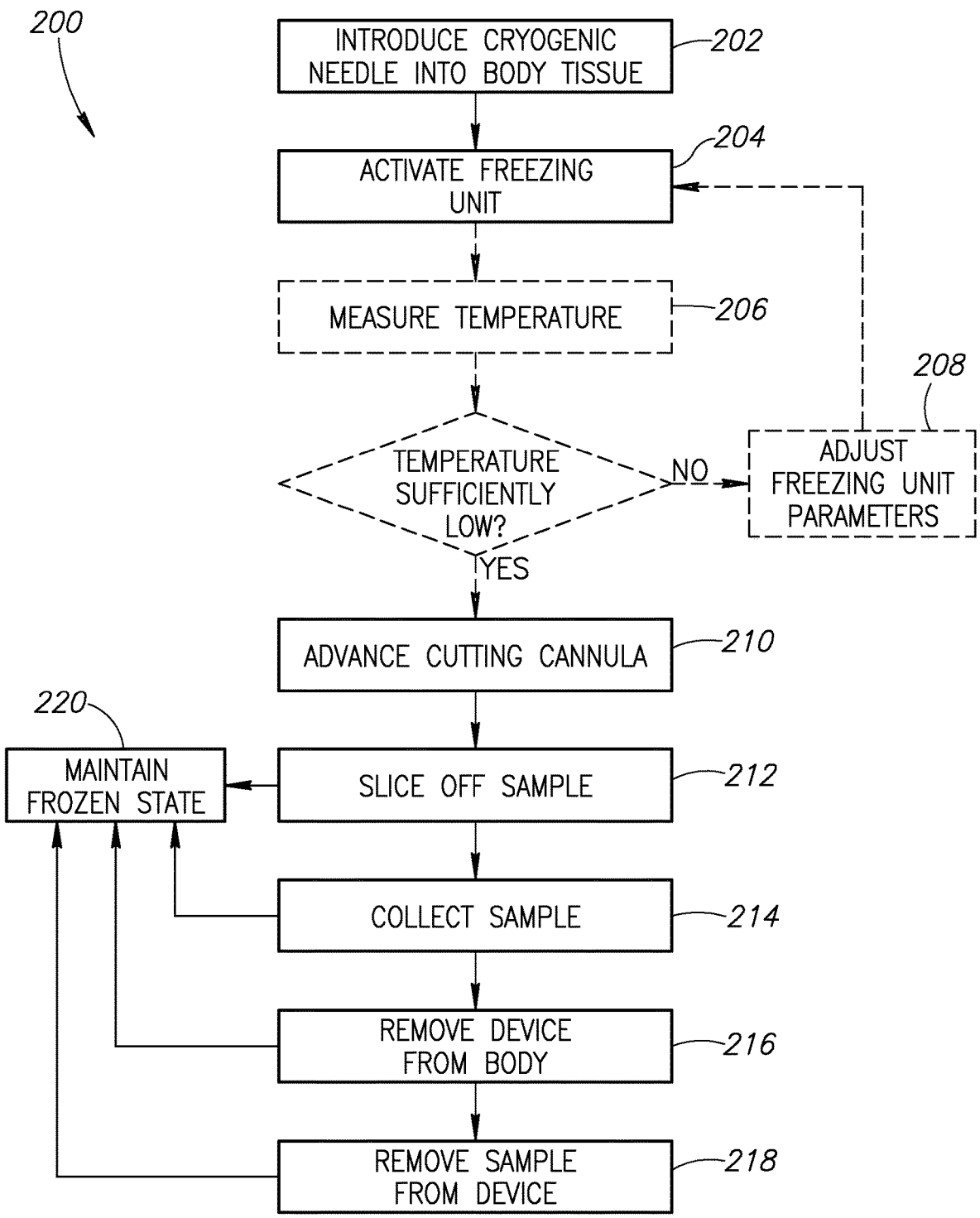
FIG. 10 is a flow-chart illustration showing the steps of a method of obtaining a biopsy sample, in accordance with embodiments of the present invention.

Reference is now made to FIG. 10, which is a flow-chart illustration showing the steps of a method 200 of obtaining a biopsy sample, in accordance with embodiments of the present invention. In a biopsy procedure using device 10, cryogenic needle 26 is introduced (step 202) into the body tissue by pushing device 10 into the body as in known biopsy procedures. Freezing unit 100 is activated (step 204). In some embodiments, first sensor 110 measures (step 206) a temperature at needle tip portion 60 or within collection compartment 30. If the temperature is not low enough, freezing unit parameters are adjusted (step 208) in some embodiments using processor 104. A range of suitable temperatures may be −10 to −50 degrees Celsius, and in some embodiments approximately −30 degrees Celsius. If more than one temperature sensor is used, the temperature of the non-frozen portion of the tissue sample can be monitored as well and provide additional input to the control system, to ensure that one part of the sample is maintained in a frozen state while another part is maintained in a non-frozen state. This can be achieved, for example, by using a heating element 114 to warm the region of non-frozen tissue or by increasing the amount of freezing substance introduced into cryogenic needle 26 to further cool the region of frozen tissue. With device 10 in place, cutting cannula 28 is advanced (step 210) over cryogenic needle 26 into the tissue. Advancement may be done manually or via a motorized mechanism or by loaded spring mechanism or any other suitable mechanism. In some embodiments, cutting cannula 28 is rotatably advanced into the tissue. In other embodiments, cutting cannula 28 is advanced translationally. A tissue sample is cut off (step 212) by the cutting cannula 28. Collecting compartment 30 then collects (step 214) the tissue sample. The entire device 10 with the tissue sample therein is then removed (step 216) from the body, and the sample is removed (step 218) from inside collection compartment 30 for pathology analysis. The frozen state is maintained (step 220) or adjusted throughout the process.

Figure 11:
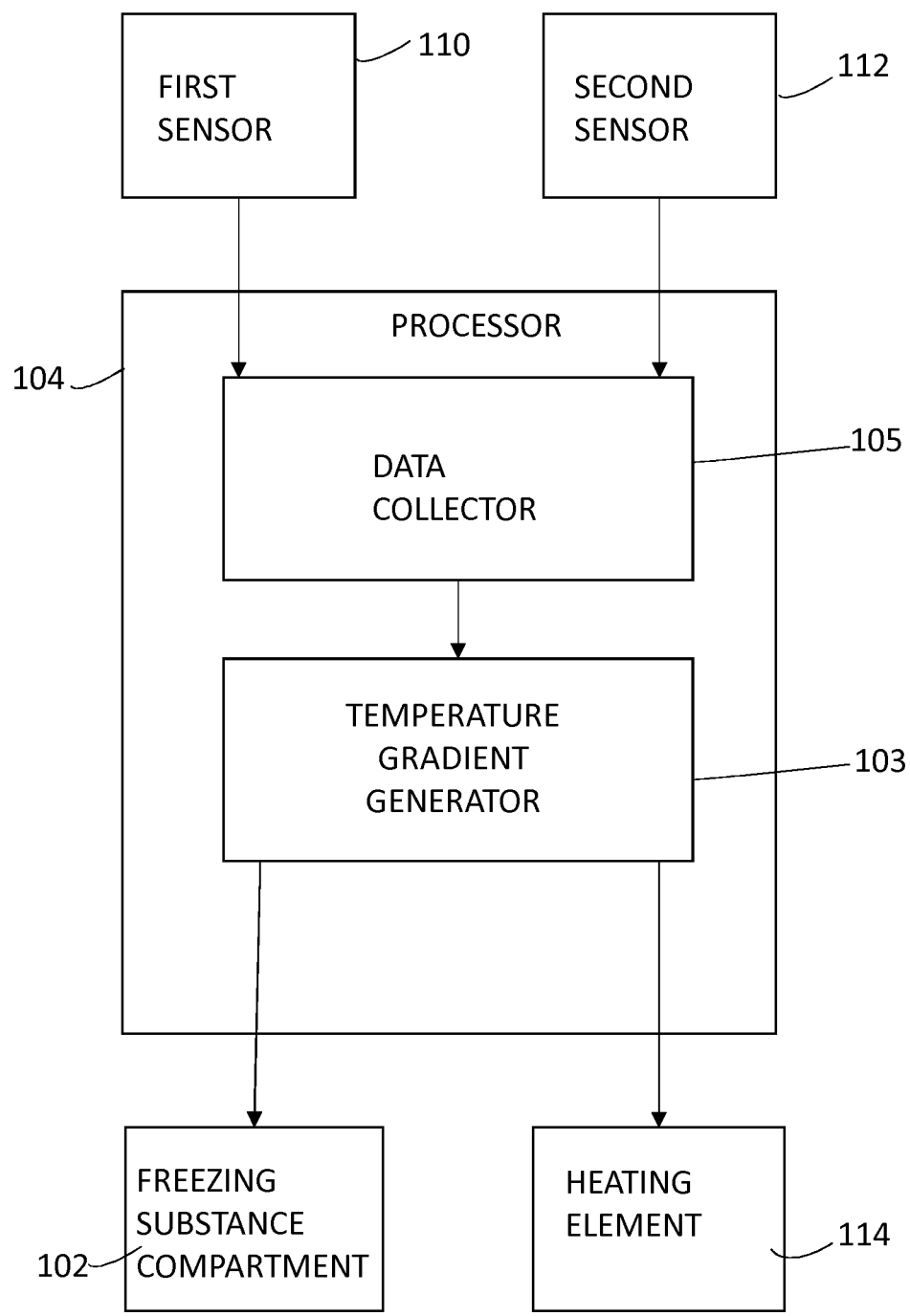
FIG. 11 is a block diagram illustration of a method of producing a temperature gradient in a tissue sample, in accordance with embodiments of the present invention.
Figure 12:
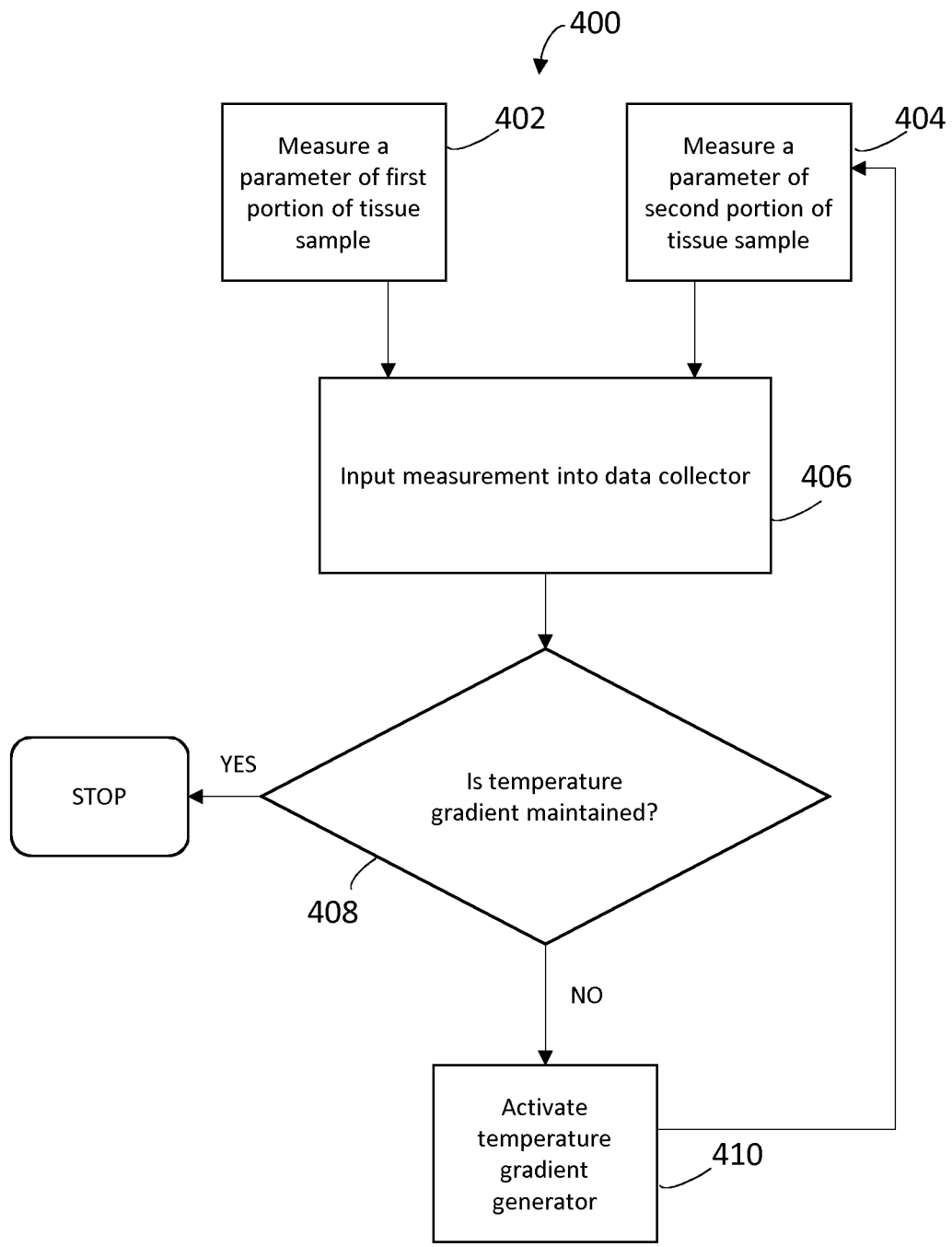
FIG. 12 is a flow chart illustration of the method of FIG. 11, in accordance with embodiments of the present invention.

Reference is now made to FIG. 11, which is a block diagram illustration, taken together with FIG. 12, which is a flow-chart illustration of a method 400 of providing a temperature gradient within a tissue sample, in accordance with embodiments of the present invention. Method 400 may be performed at any time during the procedure of obtaining a biopsy sample as described with reference to the flow chart diagram of FIG. 10, and may be repeated as necessary. First, first sensor 110 measures (step 402) a parameter of a first portion of the tissue sample, and second sensor 112 measures (step 404) a parameter of a second portion of the tissue sample. For the purpose of the present discussion, the parameter is temperature and first and second sensors 110 and 112 are temperature sensors. However, other parameters may be used as well. The measured parameters are input (step 406) into processor 104 into a data collector 105. Processor 104 then determines (step 408) if the parameters are suitable for maintaining a temperature gradient. If the parameters are suitable (e.g. the temperature in the first portion of the tissue is below freezing and the temperature in the second portion of the tissue is above freezing), then processor 104 does not activate temperature gradient generator 103. If the parameters are not suitable, the processor 104 activates (step 410) temperature gradient generator 103. This activation may include either signaling to freezing substance compartment 102 to provide additional freezing substance to cryogenic needle 26 or to provide less freezing substance to cryogenic needle 26, or signaling to heating element 114 to increase heating at a proximal end of the tissue sample or decrease heating at a proximal end of the tissue sample, or a combination thereof. Measurements are then repeated until a temperature gradient is established and maintained.

Standard biopsy procedures provide tissue samples that retain tissue histology and thus enable the analysis of tissue and cellular morphology and evaluation of biomarkers by histology based methods like IHC, FISH. In standard biopsy procedures, the evaluation of the content of biomarkers in the tissue does not involve preservation of tissue histology and is based on tissue homogenate methodologies. The cryogenic biopsy device of the present invention harvests tissue samples in a way that enables standard tissue histology analysis, histology-based biomarker analysis, and homogenate-based biomarker analysis. It is a particular feature of the present invention that the tissue harvesting is conducted after part of the tissue to be sampled is deep frozen, thus maintaining the bio-molecular profile of the intact tissue, while another part of the tissue to be sampled is maintained in a non-frozen state to enable high level histopathology analysis by high-magnification microscopy.

While certain features of the present invention have been illustrated and described herein, many modifications, substitutions, changes, and equivalents may occur to those of ordinary skill in the art. It is, therefore, to be understood that the appended claims are intended to cover all such modifications and changes as fall within the true spirit of the present invention.

What is claimed is:

1. A biopsy system comprising:
a cryogenic biopsy device, the device comprising:
a biopsy needle;
a cutting cannula positioned coaxial to said biopsy needle for providing a sliced sample of tissue;
a collection compartment for collecting the sliced sample of tissue, said collection compartment having a collection compartment proximal end and a collection compartment distal end; and
a heating element positioned on said collection compartment;
at least one sensor positioned within said collection compartment for sensing of a parameter within said collected sliced sample of tissue;
a freezing compartment for providing freezing material to said biopsy needle at a location which is greater than 7 mm away from said heating element; and
a processor configured for controlling the freezing compartment and the heating element in order to provide a temperature gradient in the sliced sample of tissue wherein the controlling is based on the sensed parameter, wherein the processor further includes a temperature gradient generator for generating the temperature gradient within said collection compartment.

2. The biopsy system of claim 1, wherein said processor is configured to increase or decrease the freezing material provided to said biopsy needle.

3. The biopsy system of claim 1, wherein said processor is configured to activate said heating element to a temperature which is less than or equal to 10 degrees Celsius.

4. The biopsy system of claim 1, wherein said at least one sensor comprises a first sensor positioned on the biopsy needle, and a second sensor positioned on a distal end of the cutting cannula in a position which is proximal to the first sensor.

5. The biopsy system of claim 1, wherein said heating element is positioned on said collection compartment proximal end and said freezing compartment is configured to provide freezing material to a tip of said biopsy needle.

6. A biopsy system comprising:
a cryogenic biopsy device, the device comprising:
a biopsy needle;
a cutting cannula positioned coaxial to said biopsy needle for providing a sliced sample of tissue;
a collection compartment for collecting the sliced sample of tissue, the collection compartment having a collection compartment distal end and a collection compartment proximal end; and
a heating element positioned on said collection compartment;
a first sensor positioned on a distal end of the collection compartment and a second sensor positioned on the cutting cannula in a position which is proximal to the first sensor, wherein said first sensor is configured to measure a first temperature, wherein said first temperature is a temperature of a distal portion said collected sliced sample of tissue and wherein said second sensor is configured to measure a second temperature, wherein said second temperature is a temperature of a proximal portion of said collected sliced sample of tissue;
a freezing compartment at a location which is greater than 7 mm away from said heating element for providing freezing material to one of said collection compartment distal end or said collection compartment proximal end; and
a processor configured for controlling the provided freezing material such that a temperature gradient is provided in the sliced sample of tissue, wherein a portion of the sliced sample of tissue is frozen and a portion of the sliced sample of tissue is non-frozen, wherein the controlling is based on the sensed first and second temperatures, wherein the processor further includes a temperature gradient generator for generating the temperature gradient within said collection compartment.

7. The biopsy system of claim 6, wherein said processor is configured to increase or decrease the provided freezing material based on the measured first and second temperatures.

8. The biopsy system of claim 6, wherein said freezing compartment is configured for providing freezing material only to said collection compartment distal end, and wherein said frozen portion of the sliced sample of tissue is located at said collection compartment distal end and said non-frozen portion of the sliced sample of tissue is located at said collection compartment proximal end.

9. The biopsy system of claim 6, wherein said freezing compartment is configured for providing freezing material only to said collection compartment proximal end, and wherein said frozen portion of the sliced sample of tissue is located at said collection compartment proximal end and said non-frozen portion of the sliced sample of tissue is located at said collection compartment distal end.

10. The biopsy system of claim 6, wherein said temperature gradient generator is configured to generate a temperature gradient of +10 degrees Celsius to −10 degrees Celsius.

* * * * *